United States Patent

Cascone

[11] Patent Number: 6,156,266
[45] Date of Patent: Dec. 5, 2000

[54] GOLD ALLOY FOR FIRING ON PORCELAIN

[75] Inventor: Paul J. Cascone, Del Mar, Calif.

[73] Assignee: Argen Corporation, San Diego, Calif.

[21] Appl. No.: 09/479,499

[22] Filed: Jan. 7, 2000

[51] Int. Cl.[7] .................................................... C22C 5/02
[52] U.S. Cl. ............................................................ 420/508
[58] Field of Search ............................................. 420/508

[56] References Cited

U.S. PATENT DOCUMENTS

| | | | |
|---|---|---|---|
| 3,136,634 | 6/1964 | Zwingmann | 75/165 |
| 3,495,978 | 2/1970 | Teets et al. | 75/165 |
| 3,716,356 | 2/1973 | Burnett | 75/165 |
| 3,981,723 | 9/1976 | Tuccillo | 75/165 |
| 4,123,262 | 10/1978 | Cascone | 75/165 |
| 4,201,577 | 5/1980 | Ingersoll et al. | 75/134 |
| 4,591,483 | 5/1986 | Nawaz | 420/463 |

*Primary Examiner*—George Wyszomierski
*Assistant Examiner*—Janelle Combs Morillo
*Attorney, Agent, or Firm*—Norris, McLaughlin & Marcus, P.A.

[57] ABSTRACT

A silverless gold alloy for dental prosthesis comprising 60–70 wt. % gold, 20–30 wt. % palladium, 0–1 wt. % of ruthenium, iridium, rhenium or of a combination thereof, as grain refiner, and the balance to 100 wt. % being indium and gallium.

3 Claims, No Drawings

GOLD ALLOY FOR FIRING ON PORCELAIN

This invention relates to a novel gold alloy useful for dental prostheses; especially for firing on porcelain.

BACKGROUND OF THE INVENTION

In dental prosthesis, crowns and bridges are generally prepared from special noble metal alloys, which are covered with porcelain. In preparing such prosthesis, however, a balance must be drawn between factors such as the necessary mechanical strength of the finished product, the strength of the bond between the alloy and the porcelain coating; and, of course, the influence of the alloy on the color of the porcelain coating.

White gold alloys are known in the art for use in preparing dental prosthesis. U.S. Pat. No. 4,123,262 and U.S. Pat. No. 3,981,723 describe white gold alloys that have met with particular success in the art. Such alloys have the desirable features of:

High strength, which allows for a broad range of appliance design and construction;

Ease of processing, in that the alloys can be processed without developing dark oxides upon heating, which had at one time been a problem due the presence of copper and/or cobalt. Modern alloys, by eliminating these elements avoid the previous problems encountered with dark oxides. The soldering which occurs during the joining of various components of complex prosthesis can also be accomplished without creating dark oxides, using the modern alloys;

moderate melting ranges, in that the modern alloys can be easily cast by a variety of methods such as torching, heat induction or resistance heating. In addition, low melting phases which might cause distortion during porcelain firing are largely eliminated in the modern alloys.

Although the known white gold alloys provide high strength, ease of processing and moderate melting ranges; it is also desirable to avoid discoloration that results from the use of otherwise desirable elements in dental alloys. Thus, for example, silver is frequently employed as one of the elements in known alloys, but the presence of silver often leads to discoloration of the porcelain which is applied over the alloy in preparing dental prosthesis.

Some porcelains have been made to include agents to prevent the discoloration caused by the silver. This method of addressing the discoloration problem has shortcomings, in that the laboratory preparing the prosthesis must monitor the silver accumulation in the porcelain-firing furnace, since the agent used can handle only a limited amount of silver before losing its effectiveness, whereupon discoloration will appear.

Thus, it is preferred to eliminate silver wherever possible.

A further problem encountered in the use of gold alloys in the preparation of dental prosthesis is that of matching the thermal expansion of the base alloy to that of the porcelain that is applied to it. The known alloys are generally classified as having either high thermal expansion coefficients or low thermal expansion coefficients, and can be used, accordingly, with high thermal expansion porcelains or low thermal expansion porcelains. Dental laboratories have therefore found it necessary to maintain supplies of different kinds of alloys, so that the proper alloy could be used in accordance with the thermal expansion properties of the porcelain to be used.

Therefore, in addition to requirement that dental alloys not deteriorate the color of porcelain coatings during processing, thermal expansion coefficients that would enable the alloys to be used together with a wide choice of porcelains would be highly desirable U.S. Pat. No. 4,123,262 represents a substantial advance in the art, in that it provides a dental gold alloy that completely eliminates the need for silver and thus avoids the porcelain discoloration that results from the presence of silver.

The alloys described in U.S. Pat. No. 4,123,262, however, have a thermal expansion coefficient of about 14 $\mu m/m/^\circ$ C. in the temperature range of 25 to 600° C., and are therefore useful primarily for porcelains having a low thermal expansion coefficient. The use of this alloy with porcelains having high thermal expansion properties does not always produce the most desirable results.

U.S. Pat. No. 3,981,723 describes an alloy that has a thermal expansion coefficient of about 14.7 $\mu m/m/^\circ$ C. in the temperature range of 25 to 600° C., and is therefore useful primarily for porcelains having a high thermal expansion coefficient, and is not desirable for use with porcelains having low thermal expansion properties. A further disadvantage of this alloy is that it includes silver in its formulation, and therefore can discolor porcelain being applied to castings made therefrom.

There is therefore a need for a dental alloy that is free of silver, and which at the same time has a thermal expansion coefficient that enables it to be used with both porcelains that have high thermal expansion properties, and those having low thermal expansion properties.

It would also be desirable if an alloy could be found which as amenable to welding by the laser-welding technique. Laser-welding machines are finding increased use in dental laboratories, but some alloys heretofore known in the art are not amenable to laser-welding. It has been found, for example, that alloys which contain tin can be difficult to weld by the laser-welding technique. The reason for this difficulty is believed to arise because, at the point where a portion of the alloy becomes molten during the welding procedure, the prevailing conditions favor the formation of tin oxide. Tin oxide, in turn, is a refractory (i.e., it is not easily reduced) and collects in the grain boundaries of the weld, rendering the resulting joint brittle.

A dental alloy which does not require the presence of tin would therefore be highly desirable.

It is therefore an object of the present invention to provide an alloy that can be used with a wide range of porcelains, while maintaining the desirable features of high strength, ease of processing, moderate melting range and a composition that does not deteriorate the color of porcelain applied thereto.

It is a further object of the present invention to provide an alloy that can be welded using a laser-welding technique, without encountering the brittleness encountered in the known tin-containing alloys.

SUMMARY OF THE INVENTION

These and other objects are met by an alloy comprising 60 to 70 Wt. % gold, 20 to 30 Wt. % palladium, 0 to 1 Wt. % of ruthenium, iridium, rhenium, or a combination thereof, as grain refiner, and the balance to 100 wt. % being indium and gallium.

DETAILED DESCRIPTION

In order to be useful with the widest possible range of porcelains, a dental alloy should have a thermal expansion coefficient of about 14.4 $\mu m/m/^\circ$ C. in the temperature range of from 25° C. to 60° C. The thermal expansion coefficient, on the other hand, is determined by the elements present in the alloy.

There are a variety of elements that could be used to achieve the desired thermal expansion coefficient, if thermal expansion coefficient were the only consideration. Many of these elements, which would otherwise be desirable from the viewpoint of their effect on thermal expansion coefficients, introduce undesirable features.

Thus, it would be desirable if Silver could be avoided, because it causes porcelain discoloration.

It would also be desirable if copper, cobalt, iron and nickel could be avoided, because they cause dark oxides.

Tin, as discussed above, is believed to cause brittle welds.

Surprisingly and unexpectedly, it has now been found that the desirable features discussed above can be achieved, and the undesirable features discussed above avoided, by an alloy comprised of 60–70 wt. % gold, 20–30 wt. % palladium, 0–1 wt. % ruthenium, iridium, rhenium or a combination thereof as grain refiner, and the remainder to 100 wt % being indium and gallium.

Preferred are alloys comprised of 60–70 wt % gold, 20–30 wt % palladium, 0.1–0.5 wt. % ruthenium, iridium or a combination thereof, 0.2–1 wt % gallium and the remainder to 100 wt % being indium.

An especially preferred alloy consists essentially of 65 wt. % gold, 26.0 wt. % palladium, 8.65 wt. % indium, 0.25 wt. % gallium and 0.1 wt. % Ruthenium.

The alloys of the present invention can be prepared by melting and mixing together the individual components, according to techniques known in the art. By way of example, and not a limitation on the invention, the individual elements can be melted by induction heating, and then mixed. Preferably, a gold-gallium alloy, or a palladium-gallium alloy is used in preparing the melt rather than pure gallium, because the gold-gallium and palladium-gallium alloys have higher melting points that pure gallium. Similarly, it is preferred to use ruthenium, Iridium or rhenium, or a combination thereof, as a pre-alloy with palladium because such a pre-alloy has a lower melting point than iridium.

EXAMPLE

An alloy having the following composition is prepared:

| ELEMENT | AMOUNT (wt. %) |
|---|---|
| Gold | 65.0 |
| Palladium | 26.0 |
| Indium | 8.65 |
| Gallium | 0.25 |
| Ruthenium | 0.1 |
| TOTAL | 100.0 wt. % |

The alloy is found to have a thermal expansion coefficient of 14.4 $\mu$m/m/° C. in the temperature range of 25 to 600° C.

The invention contemplates the making of a dental appliance or restoration by casting the alloy disclosed herein, and preferably bonding porcelain to at least a portion of its surface.

Detailed instructions for making a baked-on ceramic to gold dental appliance or restoration are given in U.S. Pat. No. 3,981,723 following the examples. Such instructions are incorporated herein by reference to such patent.

Although the present invention has been described in connection with preferred embodiments, it will be appreciated by those skilled in the art that additions, modifications, substitutions and deletions not specifically described may be made without departing from the spirit and scope of the invention defined in the claims.

I claim:

1. A dental gold alloy consisting essentially of 60–70 wt. % gold, 20–30 wt. % palladium, 0–1 wt. % ruthenium, iridium, rhenium or a combination thereof as grain refiner, and the remainder to 100 wt % being indium and gallium.

2. A dental gold alloy in accordance with claim 1 consisting essentially of 60–70 wt % gold, 20–30 wt % palladium, 0.1–0.5 wt. % ruthenium, iridium or a combination thereof, 0.2–1 wt % gallium and the remainder to 100 wt % being indium.

3. A dental gold alloy in accordance with claim 1 consisting essentially of 65 wt. % gold, 26.0 wt. % palladium, 8.65 wt. % indium, 0.25 wt. % gallium and 0.1 wt. % Ruthenium.

* * * * *